(12) United States Patent
Saeedi et al.

(10) Patent No.: US 9,965,583 B2
(45) Date of Patent: May 8, 2018

(54) INFORMATION PROCESSING METHOD

(71) Applicant: Verily Life Sciences LLC, Mountain View, CA (US)

(72) Inventors: Ehsan Saeedi, Santa Clara, CA (US); Babak Amirparviz, Mountain View, CA (US)

(73) Assignee: Verily Life Sciences, LLC, Mountain View, CA (US)

( * ) Notice: Subject to any disclaimer, the term of this patent is extended or adjusted under 35 U.S.C. 154(b) by 0 days. days.

(21) Appl. No.: 14/035,413

(22) Filed: Sep. 24, 2013

(65) Prior Publication Data
US 2014/0088881 A1    Mar. 27, 2014

Related U.S. Application Data

(63) Continuation of application No. 13/626,521, filed on Sep. 25, 2012, now abandoned.

(51) Int. Cl.
*A61B 5/00*    (2006.01)
*G06F 19/10*   (2011.01)
(Continued)

(52) U.S. Cl.
CPC .............. *G06F 19/10* (2013.01); *A61B 5/002* (2013.01); *A61B 5/1477* (2013.01);
(Continued)

(58) Field of Classification Search
CPC ... G06F 19/34; G06F 19/3418; G06F 19/3825
(Continued)

(56) References Cited

U.S. PATENT DOCUMENTS 3,958,560 A    5/1976   March
4,014,321 A    3/1977   March
(Continued)

FOREIGN PATENT DOCUMENTS

EP    0369942    5/1990
EP    686372     12/1995
(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
(Continued)

*Primary Examiner* — Gary Jackson
*Assistant Examiner* — Shirley Jian
(74) *Attorney, Agent, or Firm* — McDonnell Boehnen Hulbert & Berghoff LLP

(57) ABSTRACT

Systems, apparatus and methods including a contact lens that facilitates collection and/or processing of information associated with sensed features are provided. In one aspect, a system can include a contact lens and an analysis component external to the contact lens. The contact lens can include: a substrate; and a circuit, disposed on or within the substrate. The circuit can include: a plurality of sensors configured to sense respective features associated with a wearer of the contact lens; and a communication component configured to communicate information indicative of sensed features. The analysis component can be configured to: receive the information indicative of the sensed features; and generate statistical information based, at least, on the information indicative of the sensed features.

13 Claims, 9 Drawing Sheets

(51) Int. Cl.
 *G06F 19/00* (2018.01)
 *A61B 5/145* (2006.01)
 *A61B 5/1477* (2006.01)
 *G01K 13/00* (2006.01)
 *A61B 5/01* (2006.01)

(52) U.S. Cl.
 CPC ...... *A61B 5/14532* (2013.01); *A61B 5/14539* (2013.01); *A61B 5/6803* (2013.01); *G01K 13/002* (2013.01); *G06F 19/345* (2013.01); *G06F 19/3418* (2013.01); *A61B 5/01* (2013.01); *A61B 5/6821* (2013.01)

(58) Field of Classification Search
 USPC .................................. 600/300–301; 705/2–3
 See application file for complete search history.

(56) References Cited

U.S. PATENT DOCUMENTS

| | | | |
|---|---|---|---|
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |
| 4,401,371 A | 8/1983 | Neefe | |
| 4,463,149 A | 7/1984 | Ellis | |
| 4,555,372 A | 11/1985 | Kunzler et al. | |
| 4,604,479 A | 8/1986 | Ellis | |
| 4,612,934 A * | 9/1986 | Borkan ............... | A61N 1/36185 607/40 |
| 4,632,844 A | 12/1986 | Yanagihara et al. | |
| 4,686,267 A | 8/1987 | Ellis et al. | |
| 4,740,533 A | 4/1988 | Su et al. | |
| 4,793,353 A * | 12/1988 | Borkan ............... | A61N 1/372 607/49 |
| 4,826,936 A | 5/1989 | Ellis | |
| 4,996,275 A | 2/1991 | Ellis et al. | |
| 4,997,770 A | 3/1991 | Giles et al. | |
| 5,032,658 A | 7/1991 | Baron et al. | |
| 5,034,461 A | 7/1991 | Lai et al. | |
| 5,070,215 A | 12/1991 | Bambury et al. | |
| 5,135,297 A | 8/1992 | Valint | |
| 5,177,165 A | 1/1993 | Valint et al. | |
| 5,177,168 A | 1/1993 | Baron | |
| 5,219,965 A | 6/1993 | Valint et al. | |
| 5,260,000 A | 11/1993 | Nandu et al. | |
| 5,271,875 A | 12/1993 | Appleton et al. | |
| 5,310,779 A | 5/1994 | Lai | |
| 5,321,108 A | 6/1994 | Kunzler et al. | |
| 5,326,584 A | 7/1994 | Kamel et al. | |
| 5,336,797 A | 8/1994 | McGee et al. | |
| 5,346,976 A | 9/1994 | Ellis et al. | |
| 5,358,995 A | 10/1994 | Lai et al. | |
| 5,364,918 A | 11/1994 | Valint et al. | |
| 5,387,662 A | 2/1995 | Kunzler et al. | |
| 5,449,729 A | 9/1995 | Lai | |
| 5,472,436 A | 12/1995 | Fremstad | |
| 5,512,205 A | 4/1996 | Lai | |
| 5,585,871 A | 12/1996 | Linden | |
| 5,610,252 A | 3/1997 | Bambury et al. | |
| 5,616,757 A | 4/1997 | Bambury et al. | |
| 5,682,210 A * | 10/1997 | Weirich ............... | 348/739 |
| 5,708,094 A | 1/1998 | Lai et al. | |
| 5,710,302 A | 1/1998 | Kunzler et al. | |
| 5,714,557 A | 2/1998 | Kunzler et al. | |
| 5,726,733 A | 3/1998 | Lai et al. | |
| 5,760,100 A | 6/1998 | Nicholson et al. | |
| 5,908,906 A | 6/1999 | Kunzler et al. | |
| 5,981,669 A | 11/1999 | Valint et al. | |
| 6,087,941 A | 7/2000 | Ferraz | |
| 6,131,580 A | 10/2000 | Ratner et al. | |
| 6,193,369 B1 | 2/2001 | Valint et al. | |
| 6,200,626 B1 | 3/2001 | Grobe et al. | |
| 6,213,604 B1 | 4/2001 | Valint et al. | |
| 6,312,393 B1 * | 11/2001 | Abreu ............... | 600/558 |
| 6,348,507 B1 | 2/2002 | Heiler et al. | |
| 6,366,794 B1 | 4/2002 | Moussy et al. | |
| 6,423,001 B1 * | 7/2002 | Abreu ............... | 600/405 |
| 6,428,839 B1 | 8/2002 | Kunzler et al. | |
| 6,431,705 B1 | 8/2002 | Linden | |
| 6,440,571 B1 | 8/2002 | Valint et al. | |
| 6,450,642 B1 | 9/2002 | Jethmalani et al. | |
| 6,532,298 B1 | 3/2003 | Cambier et al. | |
| 6,544,193 B2 * | 4/2003 | Abreu ............... | 600/558 |
| 6,550,915 B1 | 4/2003 | Grobe | |
| 6,570,386 B2 | 5/2003 | Goldstein | |
| 6,576,013 B1 * | 6/2003 | Budman ............... | A61F 2/141 446/392 |
| 6,579,235 B1 | 6/2003 | Abita et al. | |
| 6,599,559 B1 | 7/2003 | McGee et al. | |
| 6,614,408 B1 | 9/2003 | Mann | |
| 6,630,243 B2 | 10/2003 | Valint et al. | |
| 6,638,563 B2 | 10/2003 | McGee et al. | |
| 6,726,322 B2 | 4/2004 | Andino et al. | |
| 6,735,328 B1 | 5/2004 | Helbing et al. | |
| 6,779,888 B2 | 8/2004 | Marmo | |
| 6,804,560 B2 | 10/2004 | Nisch et al. | |
| 6,851,805 B2 | 2/2005 | Blum et al. | |
| 6,882,940 B2 * | 4/2005 | Potts et al. ...... | 702/23 |
| 6,885,818 B2 | 4/2005 | Goldstein | |
| 6,939,299 B1 | 9/2005 | Petersen et al. | |
| 6,980,842 B2 | 12/2005 | March et al. | |
| 7,018,040 B2 | 3/2006 | Blum et al. | |
| 7,131,945 B2 | 11/2006 | Fink et al. | |
| 7,169,106 B2 | 1/2007 | Fleischman et al. | |
| 7,223,234 B2 * | 5/2007 | Stupp et al. ............... | 600/300 |
| 7,398,119 B2 | 7/2008 | Lambert et al. | |
| 7,423,801 B2 | 9/2008 | Kaufman et al. | |
| 7,429,465 B2 | 9/2008 | Muller et al. | |
| 7,441,892 B2 | 10/2008 | Hsu | |
| 7,443,016 B2 | 10/2008 | Tsai et al. | |
| 7,450,981 B2 | 11/2008 | Jeon | |
| 7,639,845 B2 | 12/2009 | Utsunomiya | |
| 7,654,671 B2 | 2/2010 | Glynn | |
| 7,699,465 B2 | 4/2010 | Dootjes et al. | |
| 7,728,949 B2 | 6/2010 | Clarke et al. | |
| 7,751,896 B2 | 7/2010 | Graf et al. | |
| 7,799,243 B2 | 9/2010 | Mather et al. | |
| 7,809,417 B2 * | 10/2010 | Abreu ............... | 600/318 |
| 7,878,650 B2 | 2/2011 | Fritsch et al. | |
| 7,885,698 B2 | 2/2011 | Feldman | |
| 7,907,931 B2 | 3/2011 | Hartigan et al. | |
| 7,926,940 B2 | 4/2011 | Blum et al. | |
| 7,931,832 B2 | 4/2011 | Pugh et al. | |
| 7,964,390 B2 | 6/2011 | Rozakis et al. | |
| 8,080,187 B2 | 12/2011 | Tepedino, Jr. et al. | |
| 8,096,654 B2 * | 1/2012 | Amirparviz et al. ...... | 351/159.4 |
| 8,118,752 B2 | 2/2012 | Hetling et al. | |
| 8,142,016 B2 | 3/2012 | Legerton et al. | |
| 8,224,415 B2 | 7/2012 | Budiman | |
| 8,446,341 B2 * | 5/2013 | Amirparviz et al. ............ | 345/7 |
| 8,608,310 B2 * | 12/2013 | Otis et al. ............... | 351/159.03 |
| 8,820,934 B1 * | 9/2014 | Ho ............... | G02C 7/04 351/159.02 |
| 8,843,321 B2 * | 9/2014 | Duke et al. ............... | 702/19 |
| 8,870,370 B1 * | 10/2014 | Otis ............... | G02C 7/04 351/159.03 |
| 8,880,139 B1 * | 11/2014 | Etzkorn et al. ............... | 600/347 |
| 8,919,953 B1 * | 12/2014 | Ho ............... | G02C 7/049 351/159.03 |
| 8,926,809 B2 * | 1/2015 | Pletcher et al. ......... | 204/403.14 |
| 8,960,898 B1 * | 2/2015 | Etzkorn ............... | G02C 7/049 351/159.03 |
| 8,965,478 B2 * | 2/2015 | Liu ............... | 600/347 |
| 8,979,271 B2 * | 3/2015 | Pletcher ............... | A61B 5/7203 351/159.02 |
| 8,985,763 B1 * | 3/2015 | Etzkorn ............... | G02C 11/00 351/159.02 |
| 9,055,902 B2 * | 6/2015 | Liu | |
| 9,358,103 B1 * | 6/2016 | Wortz ............... | A61F 2/1694 |

(56) References Cited

U.S. PATENT DOCUMENTS

| | | |
|---|---|---|
| 2002/0106709 A1* | 8/2002 | Potts et al. .................. 435/14 |
| 2002/0193674 A1 | 12/2002 | Fleischman et al. |
| 2003/0122954 A1* | 7/2003 | Kassatly ............. H04N 5/2254 |
| | | 348/335 |
| 2003/0179094 A1 | 9/2003 | Abreu |
| 2003/0208113 A1* | 11/2003 | Mault et al. .................. 600/316 |
| 2003/0225318 A1 | 12/2003 | Montegrande et al. |
| 2004/0027536 A1 | 2/2004 | Blum et al. |
| 2004/0116794 A1 | 6/2004 | Fink et al. |
| 2004/0133081 A1* | 7/2004 | Teller et al. .................. 600/300 |
| 2005/0045589 A1 | 3/2005 | Rastogi et al. |
| 2005/0119540 A1* | 6/2005 | Potts et al. .................. 600/315 |
| 2005/0221276 A1 | 10/2005 | Rozakis et al. |
| 2007/0016074 A1* | 1/2007 | Abreu .................. 600/475 |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1* | 2/2009 | Abreu .................. 600/318 |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0010571 A1* | 1/2010 | Skelton et al. .................. 607/59 |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0063371 A1 | 3/2010 | Muller et al. |
| 2010/0072643 A1 | 3/2010 | Pugh et al. |
| 2010/0103368 A1 | 4/2010 | Amirparviz et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0093288 A1 | 4/2011 | Soto et al. |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0160549 A1* | 6/2011 | Saroka et al. .................. 600/301 |
| 2011/0184267 A1* | 7/2011 | Duke et al. .................. 600/365 |
| 2011/0184271 A1 | 7/2011 | Veciana et al. |
| 2011/0184490 A1* | 7/2011 | Horsager ............ A61N 1/36046 |
| | | 607/53 |
| 2011/0224665 A1* | 9/2011 | Crosby et al. .................. 606/33 |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder |
| 2012/0109296 A1 | 5/2012 | Fan |
| 2012/0149996 A1* | 6/2012 | Stivoric et al. .................. 600/301 |
| 2012/0177576 A1 | 7/2012 | Hu |
| 2012/0201755 A1 | 8/2012 | Rozakis et al. |
| 2012/0245444 A1* | 9/2012 | Otis et al. .................. 600/345 |
| 2012/0259188 A1 | 10/2012 | Besling |
| 2013/0135578 A1* | 5/2013 | Pugh et al. ............. 351/159.39 |
| 2013/0278887 A1* | 10/2013 | Legerton .................. G02C 11/00 |
| | | 351/158 |
| 2014/0354943 A1* | 12/2014 | Pugh .................. G02C 7/022 |
| | | 351/158 |
| 2014/0354946 A1* | 12/2014 | Pugh .................. G02C 7/022 |
| | | 351/159.73 |
| 2015/0366659 A1* | 12/2015 | Wortz .................. A61F 2/1624 |
| | | 623/6.38 |

FOREIGN PATENT DOCUMENTS

| | | |
|---|---|---|
| EP | 1061874 | 12/2000 |
| EP | 1617757 | 1/2006 |
| EP | 1818008 | 8/2007 |
| EP | 1947501 | 7/2008 |
| EP | 2457122 | 5/2012 |
| JP | 05/250423 | 9/1993 |
| WO | 1995004609 | 2/1995 |
| WO | 2001016641 | 3/2001 |
| WO | 2001034312 | 5/2001 |
| WO | 2002067688 A1 | 9/2002 |
| WO | 2003065876 | 8/2003 |
| WO | 2004060431 | 7/2004 |
| WO | 2004064629 | 8/2004 |
| WO | 2006015315 | 2/2006 |
| WO | 2009094643 | 7/2009 |
| WO | 2010105728 | 9/2010 |
| WO | 2010133317 | 11/2010 |
| WO | 2011/011344 | 1/2011 |
| WO | 2011034592 | 3/2011 |
| WO | 2011035228 | 3/2011 |
| WO | 2011035262 | 3/2011 |
| WO | 2011083105 | 7/2011 |
| WO | 2011163080 | 12/2011 |
| WO | 2012035429 | 3/2012 |
| WO | 2012037455 | 3/2012 |
| WO | 2012051167 | 4/2012 |
| WO | 2012051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

(56) References Cited

OTHER PUBLICATIONS

Stauth et al., "Self-assembled single-crystal silicon circuits on plastic," PNAS, Sep. 19, 2006, pp. 13922-13927, vol. 103, No. 38.
Yao, H. et al., "A contact lens with integrated telecommunication circuit and sensors for wireless and continuous tear glucose monitoring," J. Micromech. Microeng., 2012, pp. 1-10, vol. 22.
Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.
Yao et al., "A contact lens with embedded sensor for monitoring tear glucose level," Biosensors and Bioelectronics, 2011, pp. 3290-3296, vol. 26.
Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.
Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.
Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.
Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.
Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Bionic contact lens 'to project emails before eyes,' http://www.kurzweilai.net/forums/topic/bionic-contact-lens-to-project-emails-before-eyes, Last accessed Mar. 14, 2012, 2 pages.
Tweedie, et al., "Contact creep compliance of viscoelastic materials via nanoindentation," J. Mater. Res., Jun. 2006, vol. 21, No. 2, pp. 1576-1589, Materials Research Society.
Brahim, et al., "Polypyrrole-hydrogel composites for the construction of clinically important biosensors," 2002, Biosensors & Bioelectronics, vol. 17, pp. 53-59.
Huang, et al., "Wrinkling of Ultrathin Polymer Films," Mater. Res. Soc. Symp. Proc., 2006, vol. 924, 6 pages, Materials Research Society.
Zarbin, et al., "Nanotechnology in ophthalmology," Can J Ophthalmol, 2010, vol. 45, No. 5, pp. 457-476.
Selner, et al., "Novel Contact Lens Electrode Array for Multi-electrode Electroretinography (meERG)," IEEE, 2011, 2 pages.
Liao, et al., "A 3-µW CMOS Glucose Sensor for Wireless Contact-Lens Tear Glucose Monitoring," IEEE Journal of Solid-State Circuits, Jan. 2012, vol. 47, No. 1, pp. 335-344.
Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.
Thomas, et al., "Functional Contact Lenses for Remote Health Monitoring in Developing Countries," IEEE Global Humanitarian Technology Conference, 2011, pp. 212-217, IEEE Computer Society.
Pandey, et al., "A Fully Integrated RF-Powered Contact Lens With a Single Element Display," IEEE Transactions on Biomedical Circuits and Systems, Dec. 2010, vol. 4, No. 6, pages.
Lingley, et al., "Multipurpose integrated active contact lenses," SPIE, 2009, 2 pages.
Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.
Liao, et al., "A 3µW Wirelessly Powered CMOS Glucose Sensor for an Active Contact Lens," 2011 IEEE International Solid-State Circuits Conference, Session 2, Feb. 21, 2011, 3 pages.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Lončar, et al., "Design and Fabrication of Silicon Photonic Crystal Optical Waveguides," Journal of Lightwave Technology, Oct. 2000, vol. 18, No. 10, pp. 1402-1411.
Liu, et al., "Miniature Amperometric Self-Powered Continuous Glucose Sensor with Linear Response," Analytical Chemistry, 7 pages.
Baxter, "Capacitive Sensors," 2000, 17 pages.
Lingley, et al., "A Single-Pixel Wireless Contact Lens Display," Journal of Micromechanics and Microengineering, 2011, 9 pages.
"Polyvinylidene fluoride," Wikipedia, http://en.wikipedia.org/wiki/Polyvinylidene_fluoride, Last accessed Mar. 30, 2012, 4 pages.
Murdan, "Electro-responsive drug delivery from hydrogels," Journal of Controlled Release, 2003, vol. 92, pp. 1-17.
Haders, "New Controlled Release Technologies Broaden Opportunities for Ophthalmic Therapies," Drug Delivery Technology, Jul./Aug. 2009, vol. 8, No. 7, pp. 48-53.
Singh, et al., "Novel Approaches in Formulation and Drug Delivery using Contact Lenses," Journal of Basic and Clinical Pharmacy, May 2011, vol. 2, Issue 2, pp. 87-101.
"Contact Lenses: Look Into My Eyes," The Economist, Jun. 2, 2011, http://www.economist.com/node/18750624/print, Last accessed Mar. 13, 2012, 8 pages.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.
U.S. Appl. No. 13/240,994, Titled "See-Through Display With Infrared Eye-Tracker," filed Sep. 22, 2011, 38 pages.
U.S. Appl. No. 13/209,706, Titled "Optical Display System and Method with Gaze Tracking," filed Aug. 15, 2011, 30 pages.
Adler, "What types of statistical analysis do scientists use most often?" O'Reilly Community, Jan. 15, 2010, 2 pages, http://broadcast.oreilly.com/2010/01/what-types-of-statistical-anal.html, Last accessed Sep. 4, 2012.
Bull, "Different Types of Statistical Analysis," Article Click, Feb. 4, 2008, 4 pages, http://www.articleclick.com/Article/Different-Types-Of-Statistical-Analysis/968252, Last accessed Sep. 4, 2012.
"Understanding pH measurement," Sensorland, 8 pages, http://www.sensorland.com/HowPage037.html, Last accessed Sep. 6, 2012.
"Regression analysis," Wikipedia, 11 pages, http://en.wikipedia.org/wiki/Regression_analysis, Last accessed Sep. 6, 2012.
"Statistics," Wikipedia, 10 pages, http://en.wikipedia.org/wiki/Statistics, Last accessed Sep. 6, 2012.
"Nonlinear regression," Wikipedia, 4 pages, http://en.wikipedia.org/wiki/Nonlinear_regression, Last accessed Sep. 10, 2012.
"Linear regression," Wikipedia, 15 pages, http://en.wikipedia.org/wiki/Linear_regression, Last accessed Sep. 10, 2012.
"Integrated circuit," Wikipedia, 9 pages, http://en.wikipedia.org/wiki/Integrated_circuit, Last accessed Sep. 10, 2012.
"Photolithography," Wikipedia, 8 pages, http://en.wikipedia.org/wiki/Photolithography, Last accessed Sep. 10, 2012.
"Alcohol Detection Technologies: Present and Future," American Beverage Institute, 9 pages.
Harding, et al., "Alcohol Toxicology for Prosecutors: Targeting Hardcore Impaired Drivers," American Prosecutors Research Institute, Jul. 2003, 40 pages.
Kim, et al., "Oral Alcohol Administration Disturbs Tear Film and Ocular Surface," American Academy of Ophthalmology, 2012, 7 pages.
Quick, "Color-changing electrochromic lens technology has fashion and military applications," Gizmag, Jul. 12, 2011, http://www.gizmag.com/electrochromic-lens-technology/19191/, Last accessed Apr. 12, 2012, 4 pages.
Chu, "Contact Lenses that Respond to Light," Technology Review, Nov. 10, 2009, http://www.technologyreview.com/printer_friendly_article.aspx?id=23922, Last accessed Apr. 12, 2012, 2 pages.

(56) References Cited

OTHER PUBLICATIONS

Search Report and Written Opinion for PCT/US2013/060717 dated Jan. 2, 2014.
Translation of portions of JP-05-250423.

* cited by examiner

| CHOLESTEROL INFORMATION | GLUCOSE INFORMATION | TEMPERATURE INFORMATION | PH LEVEL INFORMATION |
|---|---|---|---|
| 173 mg/dL | 39 mg/dL | 97.3 | 7.0 |
| 178 mg/dL | 31 mg/dL | 98.6 | 7.34 |
| 183 mg/dL | 37 mg/dL | 99.1 | 7.33 |
| 171 mg/dL | 43 mg/dL | 102.0 | 7.41 |

300

202 → CHOLESTEROL INFORMATION
204 → GLUCOSE INFORMATION
208 → TEMPERATURE INFORMATION
206 → PH LEVEL INFORMATION

FIG. 3

INFORMATION PROCESSING METHOD

CROSS REFERENCE TO RELATED APPLICATIONS

The present application is a continuation of U.S. patent application Ser. No. 13/626,521, filed Sep. 25, 2012, which is currently pending. The entire disclosure contents of this application are herewith incorporated by reference into the present application.

TECHNICAL FIELD

This disclosure generally relates to contact lenses that facilitate collection and/or processing of information.

BRIEF DESCRIPTION OF THE DRAWINGS

FIG. 3 is an illustration of an exemplary non-limiting table of information stored in a contact lens in accordance with aspects described herein.

DETAILED DESCRIPTION

Figure 1:
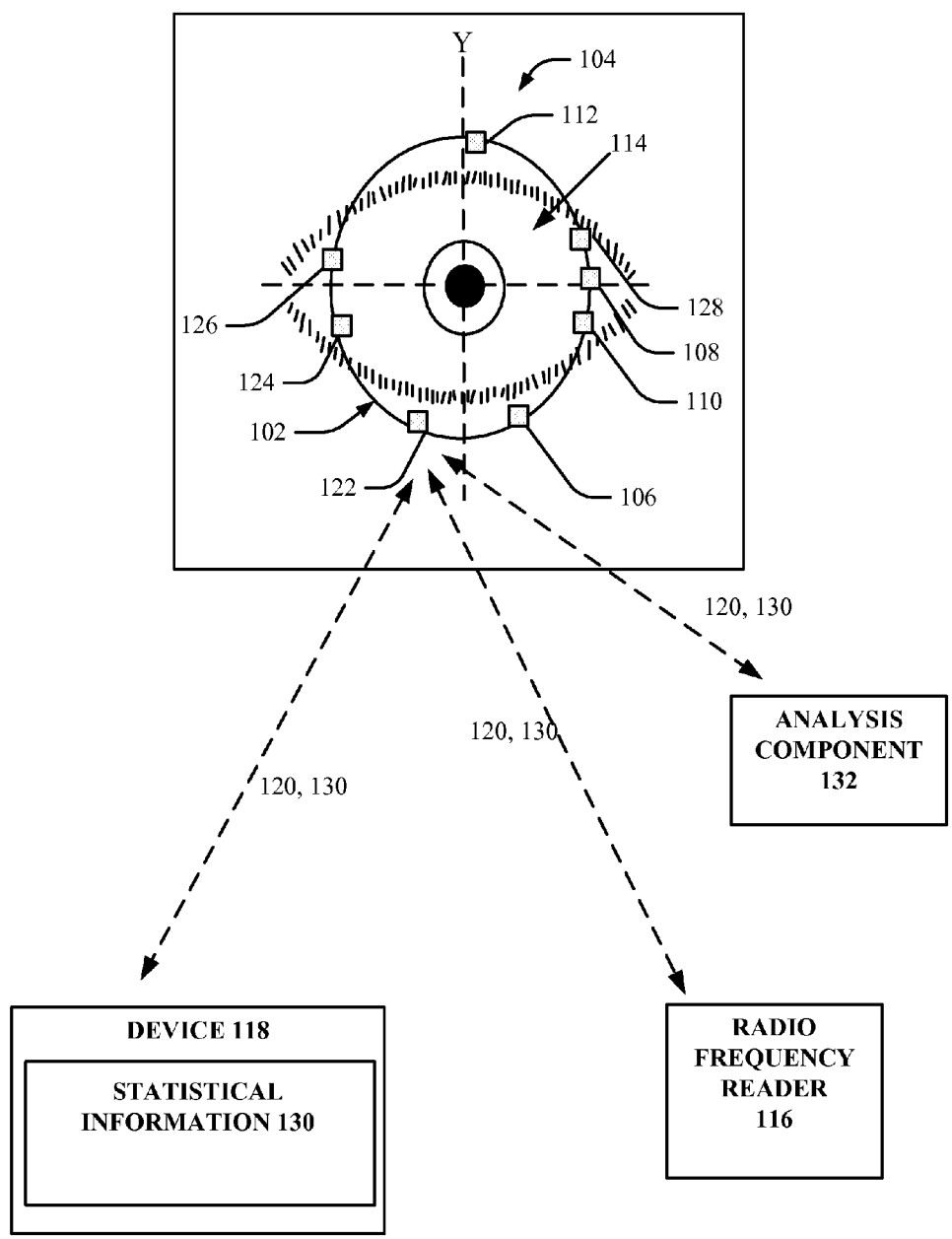
FIG. 1 is an illustration of a block diagram of an exemplary non-limiting system including a contact lens that facilitates collection and/or processing of information in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects.

Amperometry is the use of electric current or change in electric current to detect analytes in a solution. The analyte can include, but is not limited to, glucose, cholesterol, lactate, urea or the like. Specifically, amperometry is performed using amperometric electrochemical sensors with electrodes placed in close proximity to the substance being analyzed. The measurements from the electrode are based on an oxidizing or reducing reaction that occurs when the electrode is in proximity to the substance. Proper potentials applied to the electrodes cause such oxidizing or reducing reactions to occur. The resulting electrical currents can be employed in identifying the analyte in some embodiments.

Amperometric sensors require additional biosensing elements on the working electrode in order for the current-generating redox reaction to occur. One type of biosensing element is oxidase enzyme that catalyzes the oxidation of analytes by oxygen. For example, glucose oxidase can be deposited onto the sensor to enable the sensor to detect glucose.

Amperometry is performed employing an electrochemical sensor. When none of the substance being sensed touches the electrodes of the sensor, no current flows. However, when the substance being sensed touches the electrodes of the sensor, current is generated and flows. The current can be measured to determine the presence and/or concentration of the analyte in the fluid. For example, the level of concentration of the material can correspond to the measured current flow.

A number of different technologies can be employed in producing the above-referenced electrodes. For example, for noble metal thin film electrodes, vacuum deposition including sputtering and evaporation can be employed. These steps can be combined with photolithographic techniques to mask and pattern specific electrodes and connections to the electrodes. For carbon electrodes, screen printing of carbon ink can be employed.

Cholesterol is present in human eyes and tears. In some extreme cases of very high cholesterol levels in the body, for example, cholesterol accumulates and deposits around an eye lid to form tiny yellow bumps called xanthelasma palpebra. However, undesirable accumulation of cholesterol and excessive consumption of cholesterol-containing food can result in serious life-threatening conditions. For example, coronary heart diseases, cerebral thrombosis, and artherosclerosis are associated with dense accumulation of cholesterol in arterial walls.

Cholesterol concentrations are typically measured in milligrams per deciliter (mg/dL) of blood. There are three different categories of cholesterol levels: total cholesterol level, High Density Lipoprotein (HDL) cholesterol level and Low Density Lipoprotein (LDL) cholesterol level.

For total cholesterol levels, concentration less than 200 mg/dL is desirable and is considered lower risk for coronary heart disease. A total cholesterol concentration of 200 mg/dL or higher results in an elevated risk for coronary heart disease. Total cholesterol concentrations between 200-239 mg/dL are borderline high levels and cholesterol concentrations at and greater than 240 mg/dL are high cholesterol levels.

For HDL cholesterol levels, higher levels result in less risk of coronary heart disease. HDL concentrations less than 40-50 mg/dL result in high risk for heart disease, while HDL concentrations between 50-60 mg/dL are desirable.

For LDL cholesterol levels, lower levels result in less risk of coronary heart disease. LDL concentrations less than 100 mg/dL are optimal, LDL concentrations between 100-129 mg/dL are near or above optimal level, LDL concentrations from 130-159 mg/dL are borderline high level, LDL concentrations from 160-189 mg/dL are high level and LDL concentration at 190 mg/dL and higher are very high level.

Monitoring cholesterol and treatment of diseases associated with high total cholesterol are invasive and time-consuming as patients often have to visit the office of a medical provider for a health physical or procedure.

Abnormally high or low glucose levels in the body are associated with multiple health problems including diabetes mellitus and damage to organs. A normal glucose level is considered to be less than 100 mg/dL when fasting and less than 140 mg/dL two hours after eating.

The diagnosis of diabetes or pre-diabetes is based on the glucose level in the body. For example, a person can be diagnosed with diabetes mellitus if his/her glucose level is higher than 126 mg/dL after fasting for eight hours, if his/her glucose level is higher than 200 mg/dL two hours after drinking a special sugary drink offered by a medical provider and/or if the glucose level is 200 and he/she has increased urination, thirst and/or weight loss.

In conventional approaches, a daily routine involving finger sticks is required and the corresponding discomfort and inconvenience is regularly-occurring. However, a typical human tear can contain enough glucose for measurement of blood glucose level and the inconvenience and discomfort of finger sticks can be avoided or minimized in the monitoring and diagnosis of diabetes mellitus.

Potential hydrogen (pH) is the hydrogen ion level in the body. The higher the pH level, the more alkaline and oxygen rich the body. By contrast, the lower the pH level, the more acidic and oxygen deprived the body. A typical pH level range is from 0 to 14, with 7.0 being neutral. Levels above 7.0 are considered alkaline and levels below 7.0 are considered acidic.

Human blood is typically within the range between 7.35 and 7.45 with the ideal human blood pH level being slightly alkaline at a level of 7.4. Levels below or above this range can indicate disease or other health concerns (e.g., cardiovascular weakness, immune deficiency, free radical damage, stressed bladder/kidney/liver function, cancer, low energy, weight gain/loss, hormone concerns). Further, acidic blood can decrease the body's ability to properly absorb nutrients, decrease the ability of the body to repair damaged cells and detoxify heavy metals and/or can make tumor cells thrive.

The pH level in the body can be measured from numerous different bodily fluids (e.g., tear fluids, urine and saliva). Accordingly, invasive blood tests are both cumbersome and unnecessary.

The normal body temperature of a healthy, resting adult human is approximately 98.6° Fahrenheit (F). However, body temperature varies due to metabolism, with a higher metabolism resulting in higher temperature and a lower metabolism resulting in lower temperature. Time of day and day of month can also affect body temperature. For example, the body temperature is lower in the morning than in the evening. Body temperature also varies depending on the part of the body in which it is measured. Oral temperatures are typically 98.6° F., axillary temperatures are typically 97.6° F. and rectal temperatures are typically 99.6° F. The body temperature can also be measured in other areas (e.g., from the eye).

An elevated body temperature is typically indicative of illness as the body tries to fight off fungi, viruses and bacteria by raising the body temperature to a level in which germs and toxins associated with the illness cannot thrive. Accordingly, monitoring the body temperature can be an important part of preventative health.

Statistics involves the collection, organization, analysis, interpretation, and/or presentation of measured/collected information. With advances in technology, more extensive and complex computing allows massive amounts of data to be collected, stored and/or processed. Further, methods for evaluating the data are numerous.

Statistical analysis can be employed to process and/or evaluate information (e.g., levels of cholesterol, glucose, pH and/or temperature) sensed. The two main types of statistics are descriptive and inferential statistics.

Descriptive statistics includes methods for organizing and summarizing collected data. These methods include, but are not limited to, graphs, tables, charts and measurements such as averages, percentiles, and measures of variation of the data. Data mining for pattern detection, machine learning and artificial intelligence methods, regression modeling and summary statistics can be employed in descriptive statistics.

Inferential statistics is based on methods for making conclusions about data collected based on the evaluation of a sample of the data. For example, predictions can be made regarding the entire set of data. An example prediction can relate to the likelihood that a disease or illness exists based on data collected (e.g., cancer screening). Recommendations can be made to achieve or avoid predictions.

Statistical methods such as regression analysis can be employed to analyze data. Regression analysis includes techniques for analyzing different variables to determine the relationship between one or more dependent variables (e.g., cholesterol level) and independent variables (e.g., lethargy). For example, the analysis can be employed to determine how the value of a dependent variable changes when a value of one independent variable changes while keeping the values of other independent variables constant. Regression analysis can be employed for prediction and overlaps with the field of machine learning (a branch of artificial intelligence that employs algorithms to identify patterns in data and/or make predictions based on evaluated data).

Different models can be employed in regression analysis to model the relationship between two variables. Linear regression is a type of regression analysis. Linear regression models the relationship between a dependent variable (e.g., pH level) and an independent variable (e.g., information indicating general health of the wearer of the contact lens) using linear predictor functions. Unknown model parameters are estimated from the data on which linear regression is performed. Interpolation methods can be employed to perform prediction based on values within the set of collected data used for model-fitting while extrapolation can be employed to perform prediction based on values outside the set of collected data.

In linear regression models, the conditional mean of an independent variable given the dependent variable value is typically an affine function. In some cases, the median, or some other quantile of the conditional distribution of the independent variable given the dependent variable is a linear function of the dependent variable.

Non-linear regression is a type of regression analysis in which observed information (e.g., glucose concentration value) is modeled by a non-linear function. The non-linear function is a combination of the model parameters and depends on an independent variable.

Apparatus, systems and methods disclosed herein relate to contact lenses that facilitate collection and/or processing of information. The contact lens collects information from the body of the wearer of the contact lens (via sensors) and an analysis component performs statistical analysis on the collected information. An external device can power the sensors on the contact lens and can receive inputs from the wearer of the contact lens about general health feelings (e.g., whether the wearer of the contact lens is lethargic or energetic). Predictions and recommendations can be made by the analysis component based on the statistical analysis performed.

One or more of the aspects described herein can advantageously facilitate non-invasive monitoring of various body features and associated analysis, predictions and recommendations for optimal health management.

In one particular aspect, an analysis component is provided. The analysis component can include: a memory configured to store computer executable components; and a processor configured to execute the following computer executable components stored in the memory: a communication component configured to receive, from a contact lens, information indicative of features sensed on the contact lens, wherein the features sensed are features of a wearer of the contact lens; and a statistical analysis component configured to generate statistical information based, at least, on the information indicative of features sensed on the contact lens.

In an aspect, a contact lens is provided. The contact lens can include: a substrate; and a circuit. The circuit can include: a plurality of sensors configured to sense respective features associated with a wearer of the contact lens, wherein the plurality of sensors are configured to be powered by a portable radio frequency (RF) device external to the contact lens; and a communication component configured to transmit, to the RF device, at least, one of information indicative of sensed features or a recommendation based on the information indicative of sensed features.

In an aspect, a method is provided. The method can include: receiving power, at a plurality of sensors on a contact lens, from a device external to the contact lens; sensing, via the plurality of sensors, a respective plurality of features associated with a wearer of the contact lens; and transmitting, from the contact lens, information indicative of sensed features, to an analysis component configured to perform statistical analysis on the information indicative of sensed features.

In an aspect, a system is provided. The system can include a contact lens and an analysis component. The contact lens can include: a substrate; and a circuit, disposed on or within the substrate. The circuit can include: a plurality of sensors configured to sense respective features associated with a wearer of the contact lens; and a communication component configured to communicate information indicative of sensed features. The analysis component can be external to the contact lens. The analysis component can be configured to: receive the information indicative of sensed features; and generate statistical information based, at least, on the information indicative of sensed features.

Various aspects will now be discussed with reference to the figures. Turning first to FIG. 1, system 100 includes a contact lens 102 that covers at least a portion of eye 104. The contact lens 102 can be configured to sense a plurality of features of the wearer of the contact lens 102 and facilitate generation of corresponding statistical information 130, an analysis component 132 that can receive sensed information 120 from the contact lens 102 and generate statistical information 130 and/or a radio frequency (RF) reader 116 to which information 120 or statistical information 130 can be transmitted.

In some aspects, the system 100 can also include a device 118 configured to store information 120 sensed on the contact lens 102 and/or statistical information 130 generated by the analysis component 132. The device 118 can also perform various different primary functions (e.g., a smart phone, laptop or head-mounted display device that performs communication, word processing and/or display functions in addition to storage of information 120 or statistical information 130). While the analysis component 132 is shown as a separate component from the device 118, in some aspects, the analysis component 132 can be included in the device 118. In some aspects, the analysis component 132 can be included in the contact lens 102.

The contact lens 102 can include a substrate 114, sensors 106, 108, 110, 112, sensor circuitry 128 and communication component 122. In some aspects, the contact lens 102 can also include memory 124 and/or microprocessor 126. In some aspects, one or more of the sensors 106, 108, 110, 112, analysis component 132, communication component 122, memory 124 and/or microprocessor 126 can be included as part of one or more circuits on the contact lens 102. In some aspects, one or more of sensors 106, 108, 110, 112, communication component 122, memory 124 and/or microprocessor 126 can be communicatively and/or electrically coupled to one another to perform one or more functions of the contact lens 102. The components can be disposed on or within substrate 114.

The sensors 106, 108, 110, 112 can be configured to sense various features associated with a wearer of the contact lens 102. For example, sensor 106 can be configured to sense glucose information (e.g., glucose concentration and/or glucose level) associated with the wearer of the contact lens 102. Sensor 108 can be configured to sense cholesterol information (e.g., cholesterol level) associated with the wearer of the contact lens 102. Sensor 110 can be configured to sense pH level associated with the wearer of the contact lens 102. Sensor 112 can be configured to sense temperature associated with the wearer of the contact lens 102.

Glucose sensor 106 and cholesterol sensor 108 can be amperometric electrochemical sensors that detect the presence and/or concentration of glucose and cholesterol, respectively. The sensors 106, 108 can employ an oxidases enzyme to catalyze the oxidation of glucose and cholesterol by oxygen. The product can be hydrogen peroxide ($H_2O_2$). For example, glucose oxidase can be deposited onto the sensor 106 to enable the sensor 106 to perform as a glucose biosensor. Similarly, cholesterol oxidase can be deposited onto the sensor 108 to enable the sensor 108 to perform as a cholesterol biosensor. When glucose or cholesterol is sensed at sensors 106, 108, current can flow and the output current can be indicative of the level of glucose sensed by sensor 106 or the level of cholesterol sensed by sensor 108. The sensor circuitry 128 can be coupled to the sensors 106, 108 and determine the output current for the sensors 106, 108. The output current can be indicative of the concentration of the analyte in the solution.

Sensor 110 can be an electrochemical sensor that has a voltage output indicative of the pH level in tear fluid incident on the contact lens 102. In some aspects, the sensor 110 includes at least a measuring electrode, a reference electrode and a temperature sensing component. The measuring electrode can develop a potential as a function of the hydrogen ion concentration in the solution being sensed. The potential can be measured relative to the potential at the reference electrode. Because the potential at the measuring circuit can also change based on temperature changes, the potential at the measuring circuit can be adjusted based on the temperature (which is sensed by the temperature sensing component). The adjusted potential is a function of the pH level in the solution sensed. The sensor circuitry 128 can be coupled to the sensor 110 and determine the change in potential.

Sensor 112 can be a temperature sensor that changes resistance based on sensed temperature. For example, the sensing component of sensor 112 can include a resistance component (e.g., resistance thermometer) configured to sense temperature on the contact lens 102 and increase resistance with a rise in temperature or decrease resistance with a decrease in temperature. Current output from the sensor 112 can change as a result of the change in the resistance. As such, the output current can be indicative of the temperature (or change in temperature) sensed by sensor 112. The sensor circuitry 128 can be coupled to the sensor 110 and determine the output current.

Figure 2:
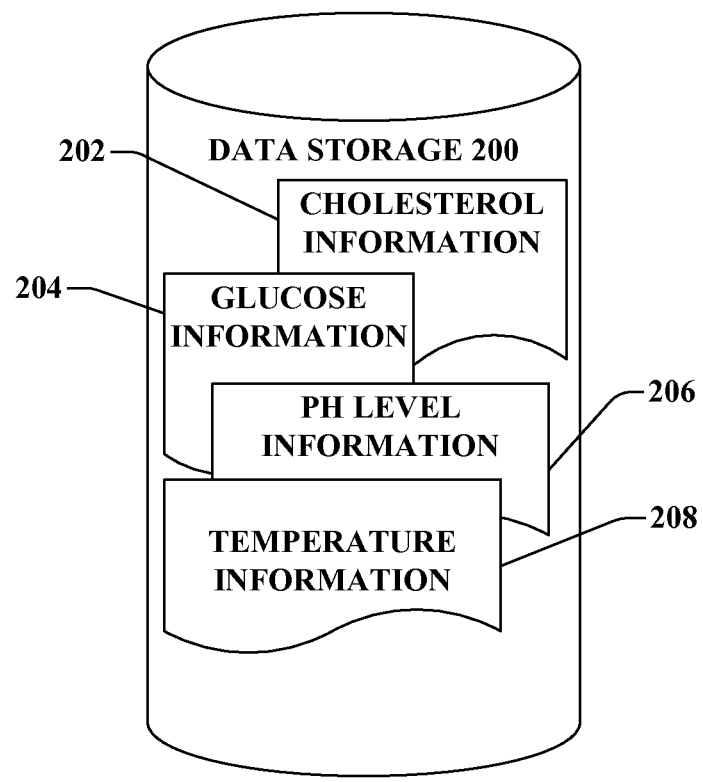
FIG. 2 is an illustration of an exemplary non-limiting data storage of a contact lens that facilitates collection and/or processing of information in accordance with aspects described herein.

The memory 124 can store information regarding cholesterol, glucose, temperature and/or pH levels/concentrations measured/sensed and/or computer-executable instructions for execution by the microprocessor 126. FIG. 2 is an illustration of an exemplary non-limiting data storage of a contact lens that facilitates collection and/or processing of information in accordance with aspects described herein. FIG. 3 is an illustration of an exemplary non-limiting table of information stored in a contact lens in accordance with aspects described herein. Memory 124 can include data storage 200 in some aspects.

With reference to FIGS. 2 and 3, in some aspects, a data storage (e.g., data storage 200) can be provided on the contact lens 102 and can store the information sensed by the sensors 106, 108, 110, 112. For example, the data storage 200 can be included as part of the memory 124 in some aspects. In some aspects, data storage 200 is not provided on the contact lens 102, but is accessible by the contact lens 102 for storage of and retrieval of information 120 and/or statistical information 130.

Data storage 200 can store glucose information 204 (e.g., glucose concentrations and/or information indicative of the level of the glucose concentration), cholesterol information 202 (e.g., cholesterol concentration and/or information indicative of the level of the cholesterol concentration), pH level information 206 (e.g., numerical pH value and/or information indicative of the level of the pH) and/or temperature information 208 (e.g., temperature value and/or information indicative of the level of the temperature).

As shown in table 300 of FIG. 3, the numerical values associated with concentrations or levels can be stored in data storage 200 as glucose information 204 (e.g., glucose concentrations and/or information indicative of the level of the glucose concentration), cholesterol information 202 (e.g., cholesterol concentration and/or information indicative of the level of the cholesterol concentration), pH level information 206 (e.g., numerical pH value and/or information indicative of the level of the pH) and/or temperature information 208 (e.g., temperature value and/or information indicative of the level of the temperature). The measured/sensed received cholesterol information 202, glucose information 204, temperature information 208 and/or pH level information 206 can be current information and/or past information. In some aspects, the information can be collected over a period of time. For example, the measured/sensed received cholesterol information 202, glucose information 204, temperature information 208 and/or pH level information 206 can be collected over a period of time (e.g., one month, six months, one week) prior to the analysis component 132 performing statistical analysis on the measured/sensed information.

The data storage 200 can be configured to store information transmitted to, received by and/or processed by the analysis component 132. For example, the data storage 200 can store glucose information 204 (e.g., current, historical and/or average glucose concentration information), cholesterol information 202 (e.g., current, historical and/or average cholesterol levels), pH level information 206 (e.g., current, historical and/or average pH levels) and/or temperature information 208 (e.g., current, historical and/or average body temperature information). In some aspects, although not shown, the data storage 200 can store statistical information (e.g., statistical information 130) received from the analysis component 132.

The values and the levels provided are merely exemplary for the purposes of illustrating the systems and methods herein and may or may not be accurate depictions of the true values, concentrations and/or levels by which the system and/or the methods operate.

The microprocessor 126 can execute computer-executable instructions to perform one or more functions of the contact lens 102. For example, in some aspects, the microprocessor 126 can convert the output current from various sensors 106, 108, 110, 112 to measured/sensed concentrations and/or levels.

In various aspects, sensors 106, 108, 110, 112 can sense various features concurrently, at non-overlapping times or at random. For example, in some aspects, the sensors 106, 108, 110, 112 can perform sensing on a single sample of fluid incident on the contact lens 102 and thereby perform sensing concurrently.

In some aspects, the sensors 106, 108, 110, 112 are remotely powered for short time intervals by device 118. For example, communication component 122 can include a radio frequency (RF) antenna (not shown) that can receive RF signals from device 118 for powering the sensors 106, 108, 110, 112 and sensor circuitry 128.

The RF signals received can enable the sensors 106, 108, 110, 112 and sensor circuitry 128 to be powered on for relatively short periods of time (e.g., 10 seconds, 20 seconds, 1 minute). When the communication component 122 receives the RF signal and the sensors 106, 108, 110, 112 and sensor circuitry 128 are powered on, the sensors 106, 108, 110, 112 can read/sense glucose, cholesterol, temperature and/or pH in the wearer of the contact lens 102, and the sensor circuitry 128 can determine various information 120 (e.g., concentrations and/or levels of the glucose, cholesterol, temperature and/or pH).

In some aspects, the communication component 122 can transmit the information 120 to a device external to the contact lens 102. For example, the communication component 122 can transmit the information 120 to device 118 for storage of the information 120. As another example, the communication component 122 can transmit the information 120 to analysis component 132 or RF reader 116.

It is to be appreciated that in accordance with one or more aspects described in this disclosure, users can opt-in or opt-out of providing personal information, demographic information, location information, proprietary information, sensitive information, or the like in connection with data gathering aspects. Moreover, one or more aspects described herein can provide for anonymizing collected, received or transmitted data.

In various aspects, device 118 can include any number of devices external to the contact lens 102 and able to communicate RF signals and receive inputs from a wearer of the contact lens 102. By way of example, but not limitation, device 118 can include a smart phone, tablet computer, laptop, head-mounted display device and/or RF reader (e.g., RF reader 116).

Figure 4:
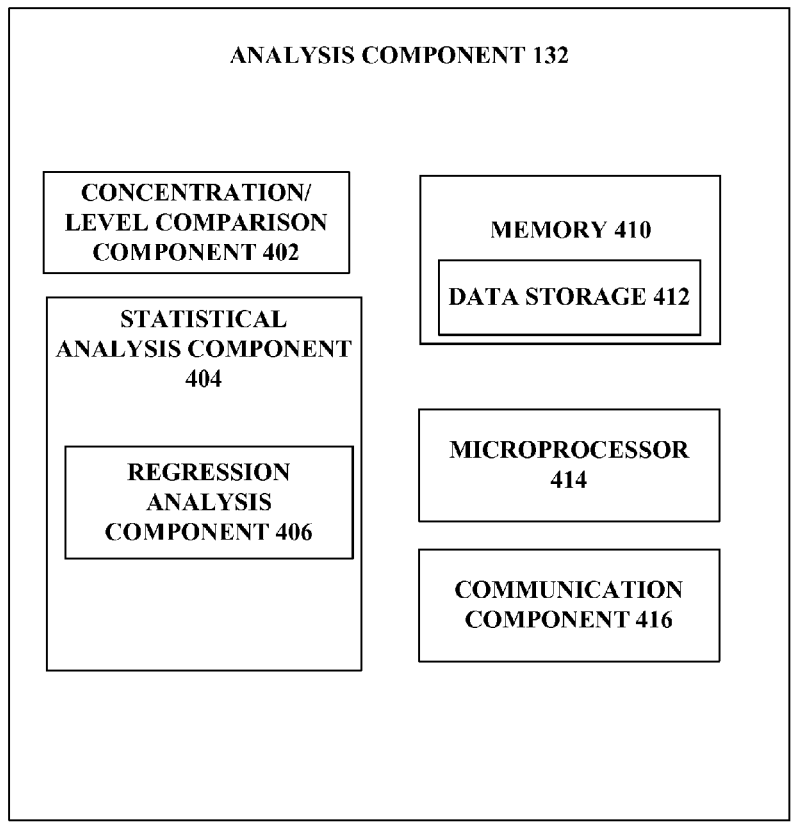
FIG. 4 is an illustration of an exemplary non-limiting diagram of an analysis component that facilitates processing of information in accordance with aspects described herein.
Figure 5:
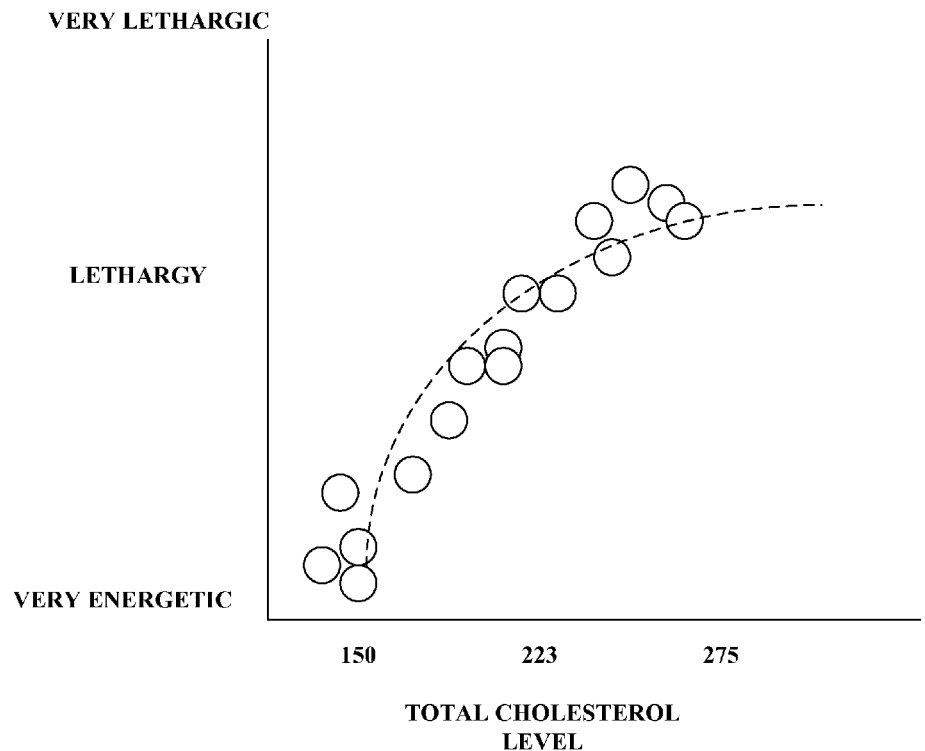
FIG. 5 is an illustration of an exemplary non-limiting graph detailing statistical information generated by an analysis component in accordance with aspects described herein.

The analysis component 132 of system 100 can be described in greater detail with reference to FIGS. 1-5. FIG. 4 is an illustration of an exemplary non-limiting diagram of an analysis component that facilitates processing of information in accordance with aspects described herein. FIG. 5 is an illustration of an exemplary non-limiting graph detailing statistical information generated by an analysis component in accordance with aspects described herein.

Turning first to FIG. 4, the analysis component 132 can include a concentration/level comparison component 402, a statistical analysis component 404, memory 410, microprocessor 414 and/or communication component 416. The concentration/level comparison component 402, statistical analysis component 404, memory 410, microprocessor 414 and/or communication component 416 can be communicatively or electrically coupled to one another to perform one or more functions of the analysis component 132.

The communication component 416 can be configured to wirelessly receive information 120 sensed by the sensors 106, 108, 110, 112 at contact lens 102. For example, with reference to FIGS. 2 and 3, the communication component 416 can received cholesterol information 202, glucose information 204, temperature information 208 and/or pH level information 206 measured by sensors 106, 108, 110, 112 and transmitted from contact lens 102.

The memory 410 can store received cholesterol information 202, glucose information 204, temperature information 208 and/or pH level information 206 and/or computer-executable instructions for execution by the microprocessor 414. The microprocessor 414 can execute computer-executable instructions to perform one or more functions of the analysis component 132. For example, in some aspects, the microprocessor 414 can facilitate statistical analysis performed by the analysis component 132.

The concentration/level comparison component 402 can compare received cholesterol information 202, glucose information 204, temperature information 208 and/or pH level information 206 with biological features information stored at data storage 412. In some aspects, the biological features information can include tables, charts and/or graphs detailing various constants/values for cholesterol, glucose, temperature and/or pH level for adults or customized for the wearer of the contact lens 102. The biological features information can also include information corresponding to the different values indicating whether a value/level is too high, too low or optimal.

In various aspects, the concentration/level comparison component 402 can determine whether the measured/sensed concentration or level is too high, too low or optimal based on the comparison between the received cholesterol information 202, glucose information 204, temperature information 208 and/or pH level information 206 and the biological features information stored at data storage 412. In some aspects, the concentration/level comparison component 402 can determine variation over time in an amount of one or more of the features in a body of the wearer of the contact lens.

In various aspects, the statistical analysis component 404 can perform any number of different types of mathematical functions for processing and/or statistical analysis of the received cholesterol information 202, glucose information 204, temperature information 208 and/or pH level information 206. In some aspects, the statistical analysis component 404 can access equations stored at the data storage 412 to perform such functions. By way of example, but not limitation, the statistical analysis component 404 can perform averaging, computation of probabilities and probability distribution functions, cumulative distribution functions, calculation of series, vector analysis, determination of percentile information or measures of variation associated with the measured/sensed information and any number of other types of mathematical operations associated with or used during statistical analysis. The generated information can be statistical information 130.

The statistical analysis component 404 can also include a regression analysis component 406. The regression analysis component 406 can receive cholesterol information 202, glucose information 204, temperature information 208 and/or pH level information 206 sensed by sensors 106, 108, 110, 112. The cholesterol information 202, glucose information 204, temperature information 208 and/or pH level information 206 (including associated qualitative or quantitative information) can considered dependent variables by the regression analysis component 406.

The regression analysis component 406 can also receive general health information descriptive of how the wearer of the contact lens 102 is feeling. For example, the wearer of the contact lens 102 can enter information at the device 118 regarding whether the wearer of the contact lens 102 is experiencing any sickness and/or the general feeling/mood of the wearer of the contact lens 102. For example, information indicative of energy level, double vision, pain, appetite can be optional information input as general health information. The information can considered independent variables by the regression analysis component 406.

The general health information can be input via voice commands/information, keyboard or touch screen input or any number of other ways that information can be input into device 118.

In various aspects, the general health information can be transmitted from the device 118 to the analysis component 132 (and/or to the contact lens 102, which can transmit the general health information to the analysis component 132). The analysis component 132 can store the information as general health information at the data storage 412 in some aspects.

The regression analysis component 406 can employ regression analysis to relate the measured/sensed received cholesterol information 202, glucose information 204, temperature information 208 and/or pH level information 206 to one of the variables entered by the wearer of the contact lens 102 as general health information (while, in some aspects, holding constant any other variables entered by the wearer of the contact lens 102). The regression analysis component 406 can perform regression analysis to identify the best models (e.g., linear models, non-linear models) to relate the measured/sensed information to the general health information input by the wearer of the contact lens 102. The regression analysis component 406 can then employ the model to predict health of the wearer of the contact lens 102.

For example, in some aspects, the regression analysis component 406 can evaluate the measured sensed received cholesterol information 202, glucose information 204, temperature information 208 and/or pH level information 206 and the general health information and apply a linear model to the variables to relate the sensed information to the general health information as described and shown with reference to FIG. 5.

Turning to FIG. 5, measured/sensed cholesterol levels can be associated with the input general health information associated with energy level of the wearer of the contact lens. The level of lethargy can be related to the measured/sensed cholesterol levels for a prediction of future health condition. As shown, the total cholesterol level of 100 was measured/sensed when the wearer of the contact lens reported a very energetic general health feeling. When the total cholesterol level increased beyond 200, the general health feeling reported by the wearer of the contact lens was lethargic. Further, increasingly high total cholesterol values over 200 corresponded to general health feelings of greater lethargy. As described herein, in a normal human adult, a total cholesterol level of less than 200 is optimal.

The regression analysis component 406 can determine a model to relate the total cholesterol level to the general health feeling and perform predictions about impending health condition and/or recommendations regarding health maintenance. For example, based on the example shown in FIG. 5, while general optimum levels are any total cholesterol levels below 200, the regression analysis component 406 can recommend that the wearer of the contact lens 102 maintain cholesterol levels close to 150 for maximum energy levels.

In some aspects, the statistical analysis component 404 can perform data mining operations for pattern recognition of the values associated with received cholesterol information 202, glucose information 204, temperature information 208 and/or pH level information 206. For example, the statistical analysis component 404 can analyze large quantities of numerical values associated with received cholesterol information 202, glucose information 204, temperature information 208 and/or pH level information 206. The statistical analysis component 404 can then perform cluster analysis by identifying similar measured/sensed values and grouping the similar values together. The statistical analysis component 404 can also perform anomaly detection to identify outliers in the group of values.

The regression analysis component 406 can employ pattern information to determine whether particular patterns of values for cholesterol, glucose, temperature and/or pH occur at particular times of day, month, for example. Cluster analysis can be employed to determine general health information that tends to be associated with particular measured/sensed values while anomaly detection can be employed to determine peculiarities in the body response (e.g., measured/sensed values that are significantly different from other measured/sensed values measured when the same/similar general health condition was noted).

As another example, in aspects wherein the wearer of the contact lens inputs information indicative of the type of food that the wearer of the contact lens 102 is eating or has eaten, the regression analysis component 406 can employ regression analysis to determine whether particular patterns of values for cholesterol, glucose, temperature and/or pH result after eating particular types of food.

The time interval between statistical analysis calculations can be static or dynamically changed. For example, if the analysis component 132 determines that the measured/sensed information indicates abnormal levels, the communication component 416 can transmit information to the contact lens 102 to update the frequency during which the contact lens 102 transmits stored information to the analysis component 132. As another example, the time interval can be pre-programmed prior to the initial use of the contact lens 102. For example, the wearer of the contact lens 102 and/or the medical provider for the wearer of the contact lens 102 can determine the time intervals between statistical analysis calculations.

In some aspects, a delay of several (e.g., 3) days may pass before the manifestation of symptoms predicted by the statistical analysis component 404. Accordingly, preventative measures and treatment can be preemptively provided.

In various aspects, the analysis component 132 can generate the statistical information 130 in real-time. For example, the statistical information 130 can be generated by the analysis component 132 as the sensors 106, 108, 110, 112 sense the features of the wearer of the contact lens 102 (and the contact lens 102 transmits the information 120 to the analysis component 132).

In other aspects, the sensors 106, 108, 110, 112 can perform sensing upon powering up (when RF signals are received at the contact lens 102), and the sensor circuitry 128 can determine the levels of the information 120 sensed by the sensors 106, 108, 110, 112. The information 120 sensed can be later stored (e.g., at the data storage 412 of the memory 410) and the analysis component 132 can perform statistical analysis on the stored information 120.

Turning back to FIG. 1, in some aspects, the communication component 122 of contact lens 102 can transmit information to the device 118 based on the information 120 sensed by the sensors 106, 108, 110, 112. For example, the communication component 122 can transmit information identifying nearby stores that sell foods high in sugar content (e.g., bakeries) if the sensor that measures glucose (e.g., sensor 106) measures/senses a low glucose level. Similarly, the communication component 122 can transmit information identifying nearby hospitals or clinics if the sensors 106, 108, 110, 112 measure severely abnormal glucose, cholesterol, pH and/or temperature levels.

In some aspects, the communication component 122 of contact lens 102 can receive statistical information 130 from the analysis component 132. The statistical information 130 can include, but is not limited to, a prediction or forecast regarding impending symptoms or medical condition, recommendations regarding nutritional intake, recommendation to schedule an appointment with a medical provider and/or identification of stores that can provide dietary choices suitable for the needs of the wearer of the contact lens 102.

Figure 6:
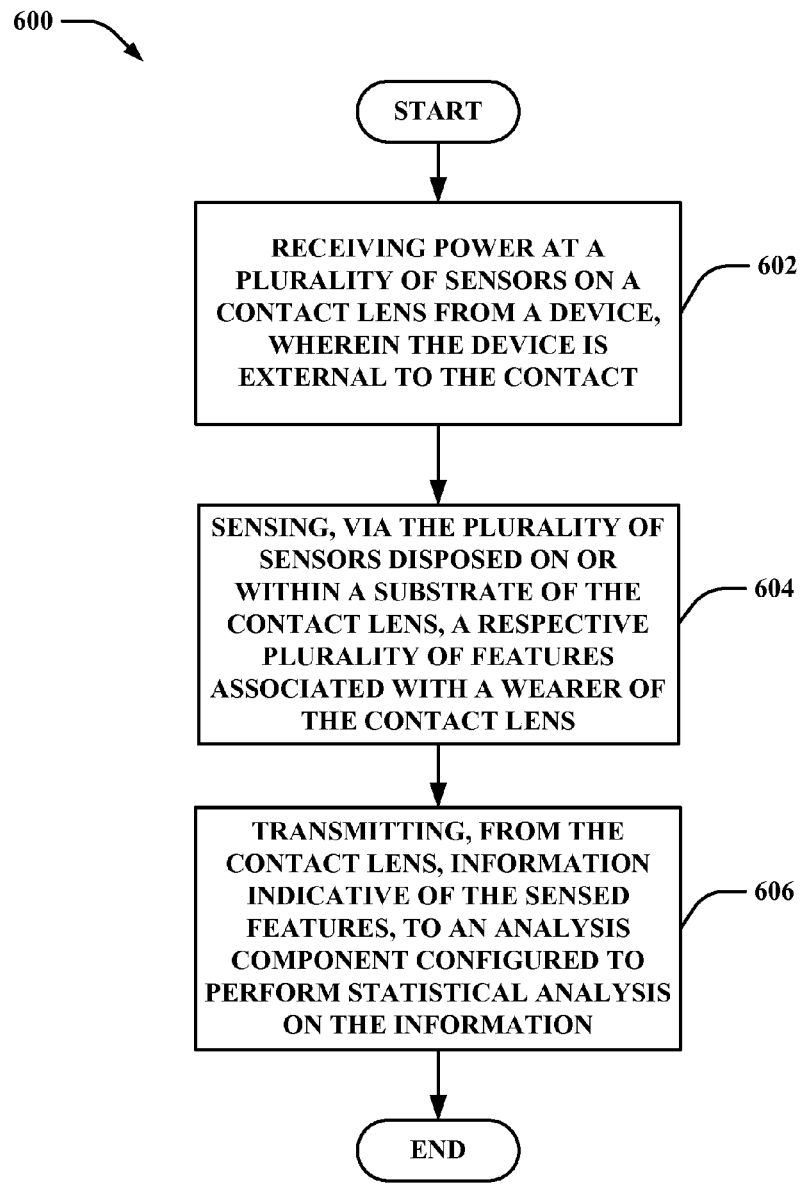
FIGS. 6 and 7 are illustrations of exemplary non-limiting flow diagrams of methods of operation for a contact lens that facilitates collection and/or processing of information in accordance with aspects described herein.
Figure 7:
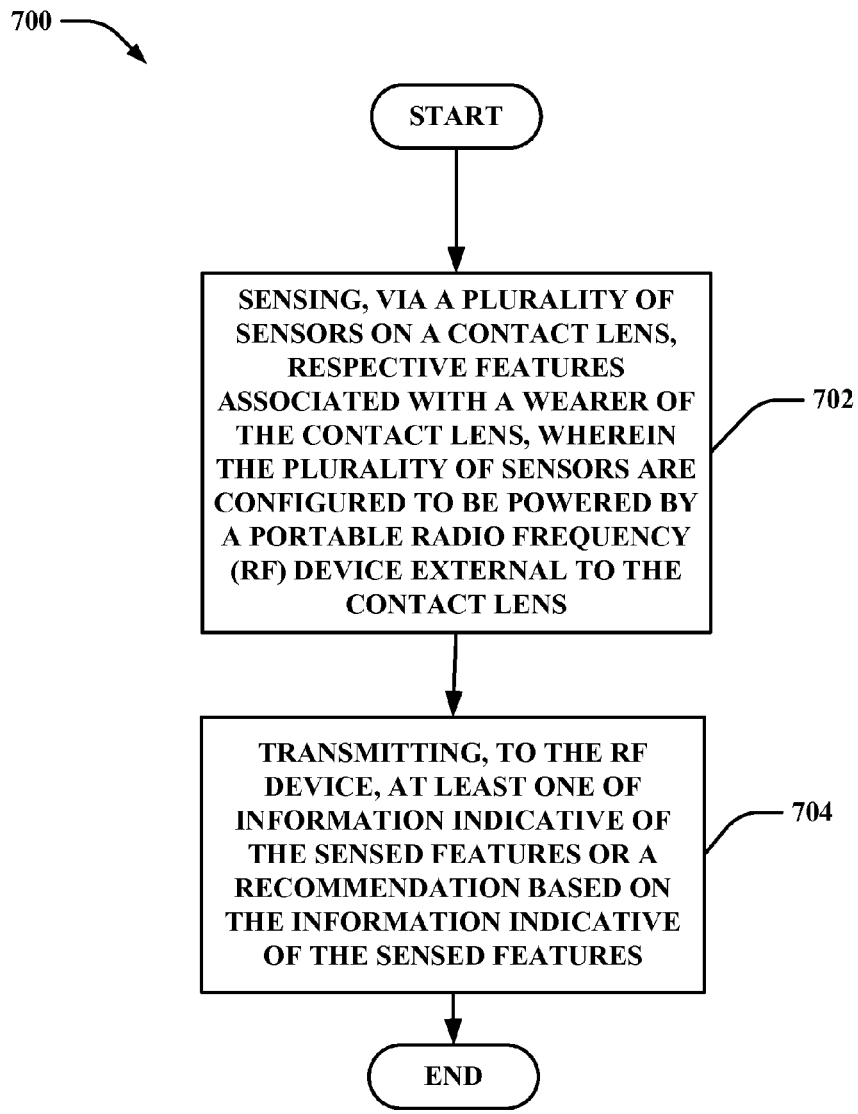

FIGS. 6 and 7 are illustrations of exemplary non-limiting flow diagrams of methods for a contact lens that facilitates collection and/or processing of information in accordance with aspects described herein. Turning first to FIG. 6, at 602, method 600 can include receiving power at a plurality of sensors on a contact lens from a device, wherein the device is external to the contact lens (e.g., using the sensors 106, 108, 110, 112). In various embodiments, the power can be received from a smart phone, head-mounted display device, or laptop associated with the wearer of the contact lens. In various aspects, the sensors can be powered intermittently upon receipt of limited bursts of power.

At 604, method 600 can include sensing, via a plurality of sensors disposed on or within a substrate of the contact lens, a respective plurality of features associated with a wearer of the contact lens (e.g., using the sensors 106, 108, 110, 112). In various aspects, the sensing can be performed while the sensors are intermittently powered. Different sensors can sense different features of the wearer of the contact lens. For example, different sensors can measure/sense glucose, cholesterol, temperature and/or pH level and/or concentration.

At 606, method 600 can include transmitting, from the contact lens, information indicative of the sensed features (e.g., using the communication component 122). The transmission can be to an analysis component configured to perform statistical analysis of the information. In various aspects, statistical analysis can include regression analysis employing the information indicative of sensed features, information about general health feelings, predictions or inferences associated with a health condition of the wearer of the contact lens, determining average values, percentages, measures of variation associated with the sensed features and the like.

Turning now to FIG. 7, at 702, method 700 can include sensing, via a plurality of sensors on a contact lens, respective features associated with a wearer of the contact lens, wherein the sensors are configured to be powered by a portable RF device external to the contact lens (e.g., using the sensors 106, 108, 110, 112). The sensors can be powered by various different types of RF devices including, but not limited to, smart phones, head-mounted display devices, laptops or the like. The device can be configured to power the sensors for limited time intervals. The sensors can then perform sensing during the time intervals during which they are powered by the device.

At 704, method 700 can include transmitting, to the RF device, at least one of information indicative of the sensed features or a recommendation based on the information indicative of the sensed features (e.g., using the communication component 122). For example, the contact lens can transmit to the RF device values such as cholesterol or glucose level/concentration, pH level and/or temperature level. In various aspects, the RF device can be associated with the wearer of the contact lens. As such, the wearer of the contact lens can be apprised of his/her body condition.

The recommendation can be an identification of dietary options (e.g., stores, bakeries, restaurants serving food that may address a deficiency or other problem determined based on the sensed features). For example, the name and location of a nearby bakery can be provided as a recommendation if a low glucose level is determined to exist for the wearer of the contact lens. As another example, the recommendation can be an identification of healthcare information (e.g., nearby hospitals, clinics, contact information for internal medicine physician or other specialists) for the wearer of the contact lens.

In some aspects, the recommendation that the contact lens can transmit to the RF device for viewing by the wearer of the contact lens can be received from an analysis component configured to perform statistical analysis on the sensed information and generate the recommendation as a result of the statistical analysis. Accordingly, sensing can be performed on the contact lens and statistical analysis can be performed by an analysis component external to the contact lens. Upon receipt of the statistical information at the contact lens, the contact lens can provide the information to the RF device.

While the aspects described herein detail the component that performs statistical analysis and the RF device as separate, in some aspects, the analysis component and the RF device can be the same component (or the analysis component can be included on the contact lens).

Exemplary Networked and Distributed Environments

Figure 8:
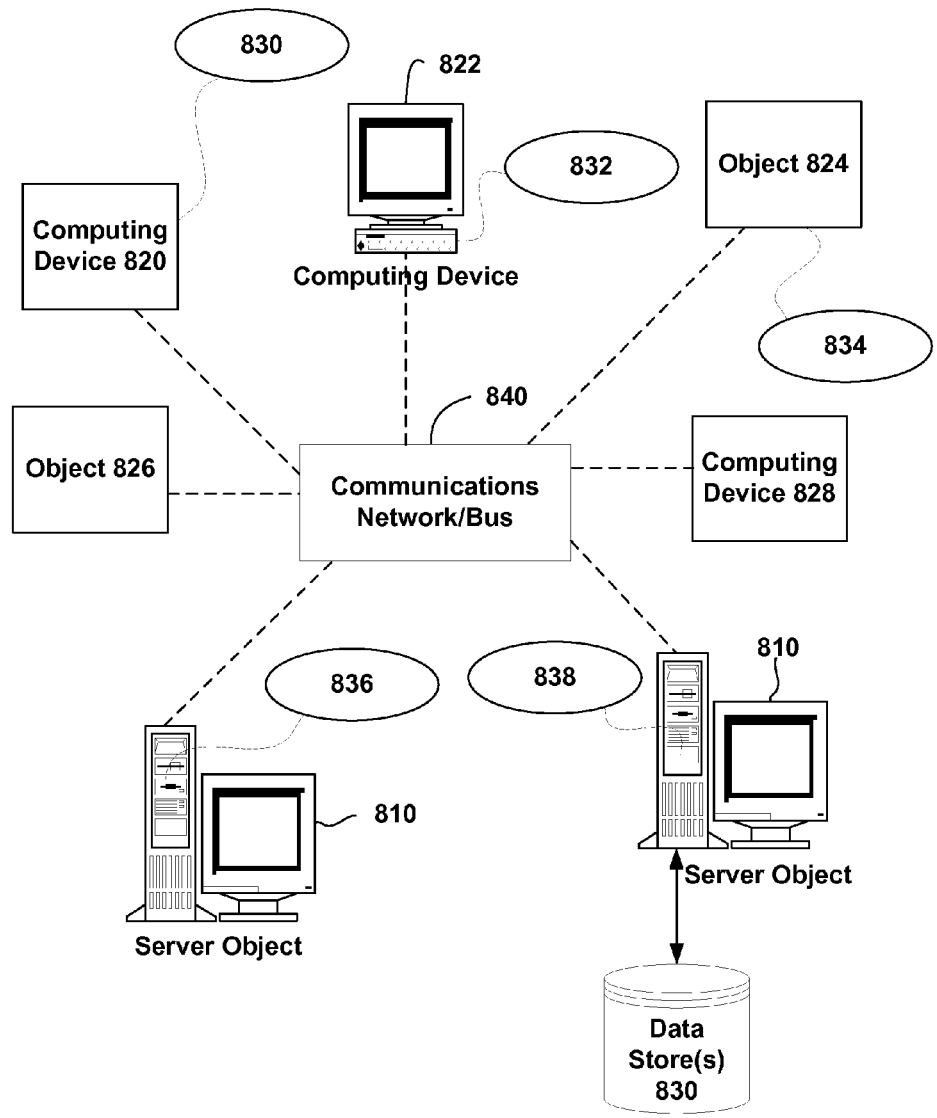
FIG. 8 is an illustration of a schematic diagram of an exemplary networked or distributed computing environment with which one or more aspects described herein can be associated.

FIG. 8 provides a schematic diagram of an exemplary networked or distributed computing environment with which one or more aspects described in this disclosure can be associated. The distributed computing environment includes computing objects 810, 812, etc. and computing objects or devices 820, 822, 824, 826, 828, etc., which can include programs, methods, data stores, programmable logic, etc., as represented by applications 830, 832, 834, 836, 838. It can be appreciated that computing objects 810, 812, etc. and computing objects or devices 820, 822, 824, 826, 828, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 810, 812, etc. and computing objects or devices 820, 822, 824, 826, 828, etc. can communicate with one or more other computing objects 810, 812, etc. and computing objects or devices 820, 822, 824, 826, 828, etc. by way of the communications network 840, either directly or indirectly. Even though illustrated as a single element in FIG. 8, network 840 can include other computing objects and computing devices that provide services to the system of FIG. 8, and/or can represent multiple interconnected networks, which are not shown.

In a network environment in which the communications network/bus 840 can be the Internet, the computing objects 810, 812, etc. can be Web servers, file servers, media servers, etc. with which the client computing objects or devices 820, 822, 824, 826, 828, etc. communicate via any of a number of known protocols, such as the hypertext transfer protocol (HTTP).

Exemplary Computing Device

As mentioned, advantageously, the techniques described in this disclosure can be associated with any suitable device. In various aspects, the data store can include or be included within, any of the memory described herein and/or any of the contact lenses described herein. In various aspects, the data store can be any repository for storing information transmitted to or received from the contact lens.

Figure 9:
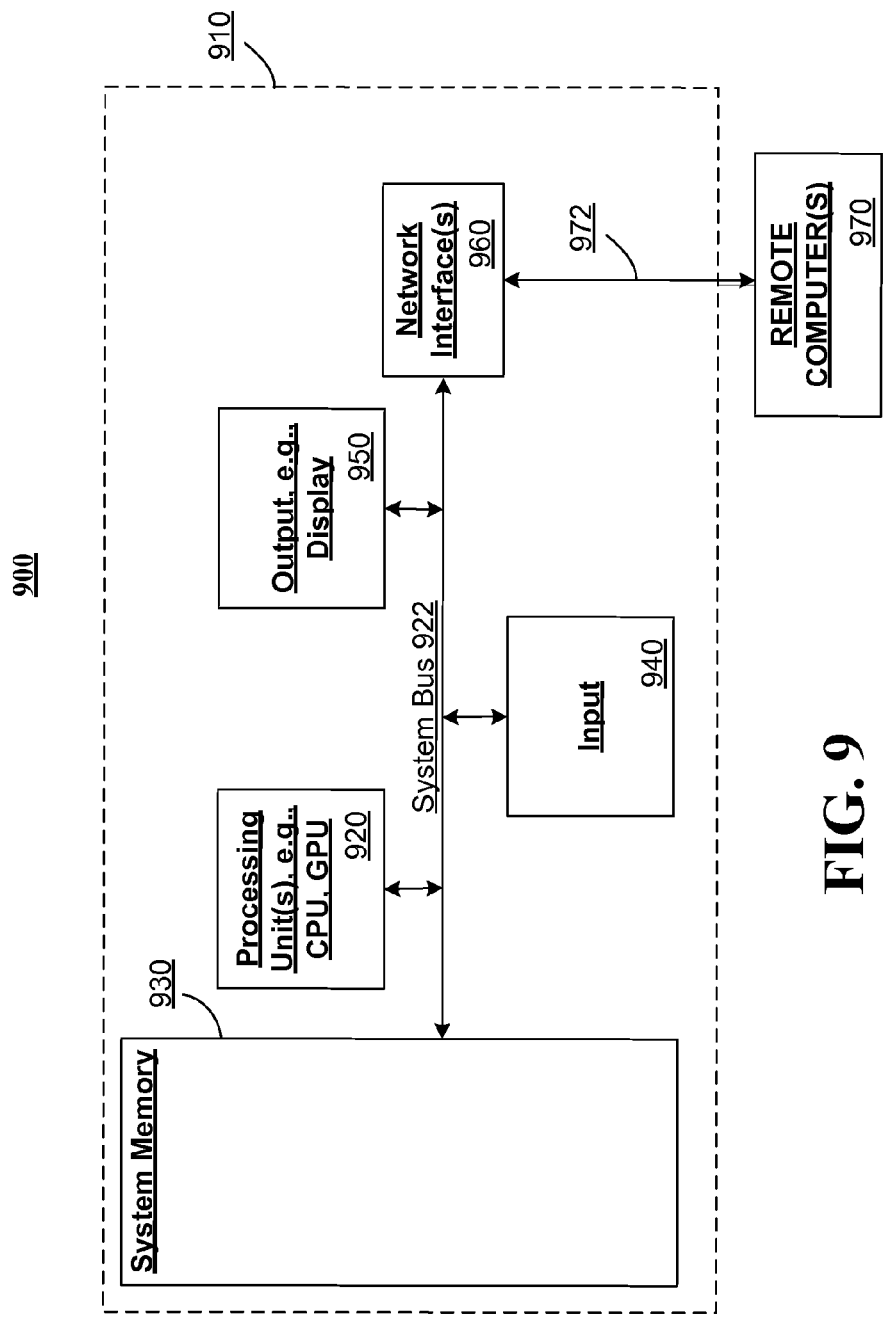
FIG. 9 is an illustration of a schematic diagram of an exemplary computing environment with which one or more aspects described herein can be associated.

FIG. 9 illustrates an example of a suitable computing system environment 900 in which one or aspects of the aspects described in this disclosure can be implemented. Components of computer 910 can include, but are not limited to, a processing unit 920, a system memory 930, and a system bus 922 that couples various system components including the system memory to the processing unit 920.

Computer 910 typically includes a variety of computer readable media and can be any available media that can be accessed by computer 910. The system memory 930 can include computer storage media in the form of volatile and/or nonvolatile memory such as read only memory (ROM) and/or random access memory (RAM). By way of example, and not limitation, memory 930 can also include an operating system, application programs, other program components, and program data.

A user can enter commands and information into the computer 910 through input devices 940 (e.g., keyboard, keypad, a pointing device, a mouse, stylus, touchpad, touch screen, motion detector, camera, microphone or any other device that allows the user to interact with the computer 910). A monitor or other type of display device can be also connected to the system bus 922 via an interface, such as output interface 950. In addition to a monitor, computers can also include other peripheral output devices such as speakers and a printer, which can be connected through output interface 950.

The computer 910 can operate in a networked or distributed environment using logical connections to one or more other remote computers, such as remote computer 980. The remote computer 980 can be a personal computer, a server, a router, a network PC, a peer device or other common network node, or any other remote media consumption or transmission device, and can include any or all of the elements described above relative to the computer 910. The logical connections depicted in FIG. 9 include a network 982, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and nonvolatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EE-PROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A contact lens, comprising:
    a substrate;
    a circuit comprising:
        a glucose sensor configured to sense glucose features associated with a wearer of the contact lens, wherein the sensor is configured to be powered by a portable radio frequency (RF) device external to the contact lens;
        a microprocessor configured to determine glucose information based, at least in part, on the sensed glucose features;
        a memory configured to store the glucose information;
        an analysis component configured to generate statistical information based, at least, on sensed glucose features, wherein the statistical information comprises information associated with a recommendation; and
        a communication component configured to transmit, to the RF device, at least, one of: glucose information or the recommendation.

2. The contact lens of claim 1, wherein the recommendation comprises information indicative of a service adapted to provide dietary options or healthcare to the wearer of the contact lens, wherein the recommendation is based, at least, on the glucose information.

3. A method, comprising:
receiving power, at a plurality of sensors on a contact lens, from a device external to the contact lens;
sensing, via the plurality of sensors, a respective plurality of features associated with a wearer of the contact lens; and
receiving, by an analysis component on the contact lens, information indicative of sensed features and general health information of the wearer of the contact lens;
wherein the analysis component comprises a microprocessor and a memory storing computer-executable instructions for execution by the microprocessor, and can:
  perform statistical analysis, based, at least in part, on a regression analysis of the information indicative of sensed features and the general health information of the wearer of the contact lens, wherein the statistical analysis is performed at a frequency;
  predict a future health condition of the wearer of the contact lens based, at least in part, on the regression analysis; and
  update the frequency at which subsequent statistical analysis is performed, wherein the frequency is updated based, at least in part, on a previously-performed statistical analysis, and the subsequent statistical analysis is performed based, at least in part, on subsequently received information indicative of features sensed on the contact lens.

4. The method of claim 3, wherein the receiving power is performed during a predefined time interval, and the sensing is performed during the predefined time interval during which the power is received.

5. The method of claim 3, wherein the plurality of features comprise at least one of cholesterol concentration, glucose concentration, temperature level or potential hydrogen (pH) level.

6. The method of claim 3, wherein the receiving power from the device comprises receiving from at least one device selected from the group consisting of smart phone, tablet computer, laptop, head-mounted display device, and radio frequency (RF) reader.

7. The method of claim 3, further comprising:
making a recommendation based, at least in part, on the information indicative of features sensed on the contact lens and the general health information of a wearer of the contact lens, wherein the recommendation comprises a recommended action to avoid a future health condition predicted by the statistical analysis component.

8. A contact lens, comprising:
a substrate; and
a circuit, disposed on or within the substrate, and comprising a plurality of sensors that can sense respective features associated with a wearer of the contact lens; and
an analysis component comprising a microprocessor and a memory storing computer-executable instructions for execution by the microprocessor, and wherein the analysis component can:
  receive, from the plurality of sensors, the information indicative of sensed features;
  generate statistical information based, at least, on a regression analysis of the information indicative of sensed features, wherein the statistical information is generated at a frequency;
  predict a future health condition of the wearer of the contact lens based, at least in part, on the regression analysis; and
  update the frequency at which subsequent statistical information is generated, wherein the frequency is updated based, at least in part, on previously-generated statistical information, and wherein the subsequent statistical information is generated based, at least in part, on subsequently received information indicative of features sensed on the contact lens.

9. The contact lens of claim 8, further comprising a radio frequency antenna configured to receive radio frequency signals to power the plurality of sensors for a predefined time interval.

10. The contact lens of claim 9, wherein the analysis component can further operate the radio frequency antenna to transmit at least one of the generated statistical information or the predicted future health condition.

11. The contact lens of claim 9, wherein the plurality of sensors are further configured to sense the respective features when the radio frequency antenna is receiving radio frequency signals to power the plurality of sensors.

12. The contact lens of claim 8, wherein the analysis component can further receive general health information input by the wearer of the contact lens and perform statistical analysis based, at least in part, on the general health information.

13. The contact lens of claim 8, wherein the analysis component is further configured to generate information indicative of a recommendation based, at least in part, on the information indicative of features sensed on the contact lens, wherein the recommendation comprises a recommended action to avoid a future health condition predicted by the statistical analysis component.

* * * * *